United States Patent
Corsini et al.

(10) Patent No.: US 12,135,262 B2
(45) Date of Patent: Nov. 5, 2024

(54) COMMINUTING DEVICE OF BIOLOGICAL MATERIAL AND RELATIVE METHOD FOR COMMINUTING AND CELLULAR PREPARATIONS

(71) Applicant: FIDIA FARMACEUTICI S.p.A., Abano Terme (IT)

(72) Inventors: Massimiliano Corsini, Capriolo (IT); Carlo Pizzocaro, Abano Terme (IT)

(73) Assignee: FIDIA FARMACEUTICI S.P.A., Abano Terme (IT)

( * ) Notice: Subject to any disclaimer, the term of this patent is extended or adjusted under 35 U.S.C. 154(b) by 487 days.

(21) Appl. No.: 17/609,924

(22) PCT Filed: May 13, 2020

(86) PCT No.: PCT/IB2020/054510
§ 371 (c)(1),
(2) Date: Nov. 9, 2021

(87) PCT Pub. No.: WO2020/230039
PCT Pub. Date: Nov. 19, 2020

(65) Prior Publication Data
US 2022/0205882 A1 Jun. 30, 2022

(30) Foreign Application Priority Data

May 15, 2019 (IT) .......................... 102019000006854

(51) Int. Cl.
*B02C 7/04* (2006.01)
*B02C 7/08* (2006.01)
(Continued)

(52) U.S. Cl.
CPC ............... *G01N 1/286* (2013.01); *B02C 7/04* (2013.01); *B02C 7/08* (2013.01); *B02C 23/36* (2013.01); *G01N 2001/2866* (2013.01)

(58) Field of Classification Search
CPC .... B02C 7/04; B02C 7/08; B02C 7/12; D21D 1/306; D21D 1/303
See application file for complete search history.

(56) References Cited

U.S. PATENT DOCUMENTS

| 1,627,506 | A | * | 5/1927 | Hamey | ..................... B02C 7/08 |
| | | | | | 241/47 |
| 1,913,540 | A | * | 6/1933 | Fritz | ......................... B02C 7/08 |
| | | | | | 241/296 |

(Continued)

FOREIGN PATENT DOCUMENTS

| CN | 106799277 | A | * | 6/2017 | ............... B02C 7/08 |
| CN | 111167561 | A | * | 5/2020 | ............... B02C 7/08 |

(Continued)

OTHER PUBLICATIONS

International Search Report (PCT/ISA/210) issued in PCT/IB2020/054510, dated Aug. 28, 2020.

(Continued)

*Primary Examiner* — Faye Francis
(74) *Attorney, Agent, or Firm* — Birch, Stewart, Kolasch & Birch, LLP

(57) ABSTRACT

A comminuting device of biological material includes a casing that contains fixed cutting elements and movable cutting elements cooperating with each other to grind biological material, a collecting chamber for ground biological material, and a partition wall adjacent to the collecting chamber. The fixed and movable cutting elements are above the partition wall together with the biological material to be ground. The collecting chamber is below the partition wall. The fixed cutting elements are in the form of elongated corners that extend radially. The movable cutting elements are in the form of elongated corners that extend radially. The partition wall is provided with wall portions. Calibrated holes are provided for the passage of biological material (Continued)

ground by the fixed cutting elements and the movable cutting elements. The collecting chamber is in connection with the outside of the casing through at least a channel.

15 Claims, 11 Drawing Sheets

(51) Int. Cl.
    *B02C 23/36*     (2006.01)
    *G01N 1/28*     (2006.01)

(56) References Cited

U.S. PATENT DOCUMENTS

| | | | | |
|---|---|---|---|---|
| 2,937,815 | A * | 5/1960 | Eirich | B02C 7/08 |
| | | | | 241/245 |
| 3,459,379 | A * | 8/1969 | Brown | B02C 7/12 |
| | | | | 241/38 |
| 4,423,845 | A * | 1/1984 | Frazier | B02C 7/12 |
| | | | | 241/261.3 |
| 5,467,931 | A * | 11/1995 | Dodd | D21D 1/306 |
| | | | | 241/296 |
| 2007/0029423 | A1 * | 2/2007 | Sanagi | B02C 7/12 |
| | | | | 241/261.2 |
| 2008/0253223 | A1 | 10/2008 | Bucher | |
| 2009/0108112 | A1 * | 4/2009 | Wakamatsu | B02C 7/17 |
| | | | | 241/47 |
| 2015/0040946 | A1 * | 2/2015 | Hofmann | B29B 17/0412 |
| | | | | 15/97.1 |
| 2016/0333305 | A1 | 11/2016 | Pilkington et al. | |
| 2018/0251942 | A1 * | 9/2018 | Gottschalk | F16L 21/03 |
| 2021/0100398 | A1 * | 4/2021 | Cha | A47J 42/20 |
| 2023/0190042 | A1 * | 6/2023 | Brogli | B02C 7/12 |
| | | | | 241/260 |

FOREIGN PATENT DOCUMENTS

| | | | | | |
|---|---|---|---|---|---|
| CN | 113477328 | A | * | 10/2021 | ............ B02C 7/12 |
| CN | 114377780 | A | * | 4/2022 | ............ B02C 7/08 |
| CN | 116713058 | A | * | 9/2023 | ............ B02C 7/08 |
| EP | 0 720 513 | A1 | | 7/1996 | |
| KR | 101529716 | B1 | * | 6/2015 | ............ B02C 7/12 |
| WO | WO 95/09051 | A1 | | 4/1995 | |
| WO | WO-2005030659 | A1 | * | 4/2005 | ........ B02C 19/0018 |
| WO | WO 2016/097960 | A2 | | 6/2016 | |

OTHER PUBLICATIONS

Written Opinion of the International Searching Authority (PCT/ISA/237) issued in PCT/IB2020/054510, dated Aug. 28, 2020.

* cited by examiner ated on
COMMINUTING DEVICE OF BIOLOGICAL MATERIAL AND RELATIVE METHOD FOR COMMINUTING AND CELLULAR PREPARATIONS

FIELD OF THE INVENTION

The present invention relates to a device adapted to comminute biological material and relative method for comminuting and cellular preparations.

The present invention falls within the technical field of devices and methods for comminuting and grinding biological material, such as animal and plant tissues, for several and different objects and applications.

In the state of the art it is in fact well known comminuting a biological material or tissue for applications for instance in biological research, clinic diagnosis and screening. Comminuting devices are therefore used to obtain samples and specimens of comminuted cells or cellular nuclei to be submitted to medical tests, such as a biopsy, or to analyse RNA, DNA, proteins or lipids, as well as in regenerative medicine in order to concentrate stem and/or pluripotent cells, such as mesenchymal stem cells. Regenerative medicine substantially aims at providing necessary elements for an in vivo reparation of the human body, i.e. at providing substitutes and/or aids able to integrate with the human being, besides stimulating and supporting the human body intrinsic ability to regenerate and heal. In such field stem cells, i.e. non-specialized primitive cells, which have the ability to transform into other types of body cells, are used. Stem cells can be from adult subjects, and in this case they are non-specialized pluripotent cells, i.e. cells able to specialize only in some types of cells. In particular human mesenchymal stem cells are presently considered as a particularly interesting instrument for regenerative medicine development in various fields, such as bone and cartilaginous tissue reparation, myocardial tissue, vascular tissue and tissue having endocrine function. These cells have the ability to self-renovate at a very high growth rate and have wide-spectrum differentiating properties. Such cells can be obtained from the bone marrow and alternative sources, such as, dental pulp, umbilical cord and placenta, adipose tissue.

More generally it is thus perceived the need for efficient devices which enable to comminute biological material and obtain samples and specimens to be tested and analysed in the laboratory to obtain data and information concerning such material, to be used for research purposes or to make a diagnosis and/or in the field of specific medical therapies, as well as to be used in regenerative medicine. The prior art already describes systems and devices adapted to comminute biological material, among which it is mentioned for exemplary purposes the triturator device disclosed in EP0720513, corresponding to WO95/09051, which comprises a cylindrical container defining an upper chamber that receives the biological material to be ground; a fixed cutting member, arranged transversally in such chamber and consisting in a perforated plate and a rotor, mounted in the chamber, with a grinding element in the form of helicoidal blade.

Another example of known comminuting system is disclosed in document WO2016/097960 that provides a rotor which cooperates with a pierced comminuting grid, where the elements characterizing the grid are microholes with size or diameter D ranging between 70 and 80 microns.

A device such as the one disclosed in EP0720513 or in WO2016/097960, carries out comminuting through the presence of microholes that "tear" or "lacerate" the biological material to be comminuted and thus tends to deteriorate it; as it can be seen in FIG. 2 of EP0720513 and in FIG. 2 of WO2016/097960 comminuting occurs through the cooperation between a rotating element and a fixed pierced disc (in particular the holes of the disc have cutting edges) and such cooperation results into "tear" or "laceration". Furthermore, it entails the formation of cellular "grafts", namely non-homogeneous pieces of biological material, with different shape and dimensions. Finally, WO2016/097960 obtains thread and pellet mixtures of different dimensions (in any case able to pass through the grid holes) and the cellular suspensions obtained from non-homogeneous grafts, statistically, do not lead to a high percentage of cell leakage.

Further comminuting devices for biological materials are disclosed for exemplary purposes in US2008/0253223, US2004/0252582 and EP2220209, all of them comprising in any case rotating blade systems or comminuting grids which thus have similar drawbacks as those reported for EP0720513 or WO2016/097960. The object of the present invention is therefore to identify a device that overcomes the drawbacks of the prior art and that allows to make biological material grafts homogeneous as for shape and dimensions.

DETAILED DESCRIPTION

The object of the present invention is therefore a comminuting device such as that specified in claim 1.

A further object is a method for comminuting biological material according to claim 14.

The comminuting device, adapted to comminute a biological material to obtain samples or specimens to be tested, according to the present invention is particularly advantageous as it performs an extremely precise, clean and homogeneous cut, obtaining cellular grafts with substantially homogeneous shape and dimensions.

The cellular grafts thus obtained, thanks to their homogeneity, enable to obtain cellular preparations formed from a number of cells (leaked from the graft itself) statistically higher than cellular preparations obtained with the devices and methods of the prior art.

Further characteristics and advantages of the present invention will be more evident from the following detailed description of some preferred embodiments thereof made with reference to the appended drawings.

In such drawings.

Figure 1:
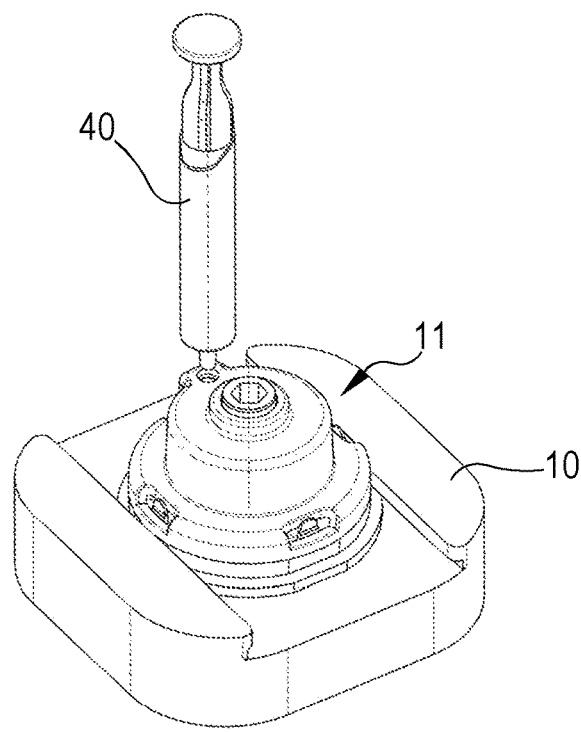
FIG. 1 is a perspective view of a comminuting device of biological material according to the invention arranged on an anti-rotation block during its use.
Figure 2:
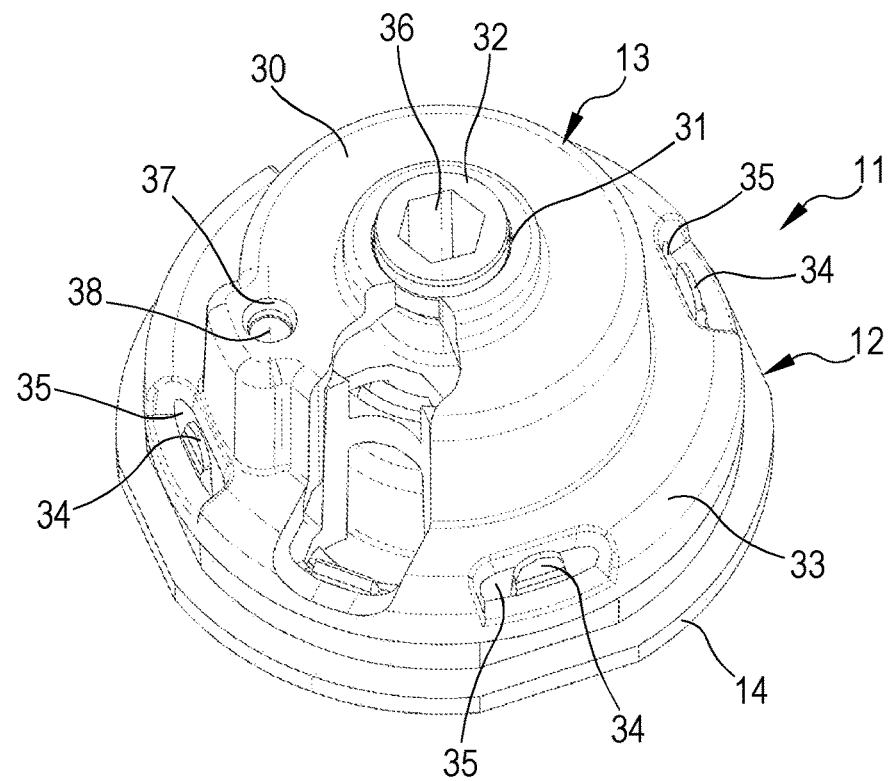
FIG. 2 is a perspective view of a first embodiment of a comminuting device of biological material according to the invention partially cut-out so as to show at least partially the inside thereof.

With reference to the Figures, a comminuting device adapted to comminute biological material is shown, indicated in its entirety by 11 in a general embodiment thereof. Such a device is usually used to carry out comminuting of a biological material to obtain samples or specimens to be analysed for various uses and is for example arranged on an anti-rotation block 10, also called "base", (which is not a strictly necessary component for the operation of the device) during its use.

The biological material 11 can generally be connective, cartilaginous, adipose, muscle, bone (and periosteum), cutaneous, skin and/or epidermal tissue and/or come from the sculp with possible skin, umbilical, placental annexes, and so on. Such biological material 11 can be, for example, sampled directly in the operating room, submitted to comminuting in the comminuting device according to the present invention, and thus carried with a suitable solvent, saline solution, isotonic water, culture medium, biodegradable, synthetic, natural and/or half-synthetic polymer, or can be used with fibrin glue or scaffold of different nature for a three-dimensional support, and so on.

In alternative, the biological material submitted to comminuting in the comminuting device according to the present invention, can be cultured with the aid of enzymes, in a medium which can contain specific trophic factors adapted to promote differentiation of possibly present mesenchimal cells (this obviously depends on the nature of the comminuted tissue) vs a specific cellular tissue, or in a culture medium containing specific trophic factors which stimulate proliferation of cells that propagate from the graft and secure survival thereof, in order to obtain either a non-differentiated mesenchimal cellular preparation, or submitted to differentiation, in alternative a preparation of non-mesenchimal cells belonging to a specific cellular tissue, to be grafted into the tissue.

Preliminary tests performed on biological tissue samples, submitted to comminuting by the comminuting device according to the present invention, show how efficient the device is in comminuting the biological tissue, for example skin or dermal, widely preserving the cell vitality among comminuted fragments, as shown by the proliferation ability of cells thus cultured.

The comminuting device according to the present invention can be disposable or can be used again to prepare samples relative to the same patient, for example for treating large burns.

Such device can have a variable volume, preferably from 5 to 15 ml, depending on the quantity of biological material to be comminuted. For exemplary purposes a 5 ml volume comminuting device can be employed to comminute skin tissue to be used in regenerative medicine, for scalp transplant and hair re-growth.

A 15 ml non-disposable comminuting device can be employed to comminute biological material for preparing cellular suspensions to be employed for treating large burns, healing ulcers and injures of different type.

The comminuting device according to the present invention allows to obtain comminuting of either cellular clusters, and single cells: the presence of the organised structures of small cellular clusters actually enables a tissue regeneration that is more rapid than culturing single cells.

In the following description the terms comminute or grind, as well as comminuted or ground, are independently used to define the same operation and the same treatment.

In particular, such a comminuting device 11 comprises a casing containing fixed and movable cutting elements cooperating with each other to grind biological material, wherein such fixed and movable elements are arranged above a partition wall which defines an underlying collecting chamber of the aforesaid biological material, once cut as desired. As said such collecting chamber is arranged below the aforesaid fixed and movable cutting elements and the aforesaid partition wall which is provided with wall portions in which calibrated holes are provided for the passage of the ground biological material.

In particular, in the figures the casing comprises an inner box-shaped body 12 and an outer box-shaped body 13, both substantially cylinder-shaped, that can be associated with each other. In particular the inner box-shaped body 12 comprises in a first part a base 14, with a circular plate, centrally provided with a camber 15, facing the upper outer body and facing the inside. In a second part the inner box-shaped body 12 comprises a hollow cylindrical element 16 also provided with a flange 17, radially facing the outside and obtained at an end of the cylindrical element 16 facing the base 14. The base 14 can be associated to the flange 17 and it is constrained thereto by means of snap-on elements 18 in form of tabs. The tabs 18 extend from the base 14 and are inserted into slits 19 provided in the flange 17. Around the camber 15 of the base 14 an annular housing 20 is obtained adapted to receive an O-ring 21 that, when engaged with a lower surface of the flange 17, realises the mentioned collecting chamber of the biological material, once cut.

In a first embodiment of FIGS. 2 to 10, in an inner intermediate portion of the cylindrical element 16 a partition wall or surface 22 is arranged which consists of sectors alternatively providing sectors 23 provided with a number of calibrated holes 23' and sectors 24 provided with concentric arc-of-a-circle teeth 24'. Either the sectors 23 provided with a number of calibrated holes 23' and sectors 24 provided with concentric arc-of-a-circle teeth 24' converge centrally towards a central circular seat 25 and face a rotor 27 housed and being part of the inner box-shaped body 13; the edges of teeth 24' (for example triangle- or trapezoid- or wave-shaped) constitute fixed cutting elements.

Said calibrated holes have a diameter ranging from 100 to 500 μm, preferably ranging from 200 to 400 μm, more preferably equal to 300 μm.

Such central circular seat 25 identifies a housing for a shaft piece 26 that extends from the aforesaid rotor 27. The rotor 27 provides in a surface thereof facing the partition wall 22 of the cylindrical element 16 a number of sectors 29 provided with concentric arc-of-a-circle teeth 29' where such sectors 29 are complimentary (or substantially complimentary) with sectors 24 provided with arc-of-a-circle teeth 24' of the partition wall 22 of the cylindrical element 16; the edges of teeth 29' (for example triangle- or trapezoid- or wave-shaped) constitute movable cutting elements.

Thereby, fixed sectors 24 and movable sectors 29, precisely rotating (with the rotor), are complimentary (or substantially complimentary) with each other cooperating with each other, and thanks to their cutting elements which are in turn complimentary (or substantially complimentary) with each other, grind the biological material placed in advance at the sectors 23;

In general, the distance between the fixed cutting elements and the movable cutting elements determines the average dimension of the ground biological material that can later pass through the calibrated holes only when the material dimension is compatible with the dimension of the holes; namely the pierced wall serves as a "calibrated sieve".

It can be stated that the fixed cutting elements (for example elements 24' and as will be seen later also elements 124') have the shape of elongated corners that extend radially; in particular, they extend radially and for example for a length of 1-10 cm, preferably for a length of 2-5 cm. Preferably, the fixed cutting elements comprise one or more rectilinear corner sections and in particular consecutive.

It can be stated that the movable cutting elements (for example elements 29' and as will be seen later also elements 129') have the shape of elongated corners that extend radially; in particular, they extend radially and for example for a length of 1-10 cm, preferably for a length of 2-5 cm. Preferably, the movable cutting elements comprise one or more rectilinear, and in particular consecutive, corner sections.

The comminuting device can be made using any plastic material and medical-grade super-polymer.

According to the embodiment of FIGS. 2-10, the rotor 27 with its cutting elements is made in a single piece for example of a plastic material and the partition wall 22 with its cutting elements is made in a single piece for example of plastic material; this embodiment is in particular for grinding "soft" material.

The base 10 can be made of a plurality of materials, for example plastic, rubber, metal (in particular steel and/or aluminium).

The outer box-shaped body 13, as said substantially cylinder-shaped, can be arranged to surround at least partially the inner box-shaped body 12 which, in a first end thereof closed by a wall 30, provides an axial central hole 31 that defines a housing seat and rotation of a shank 32 of the rotor 27.

Furthermore, the outer box-shaped body 13 provides at the other end thereof a shaped flange 33 radially protruding outwards and such to abut the base 14, with circular plate.

It must be noted that the flange 17 of the cylindrical element 16 also provides snap-on elements 34 in form of tabs. Such additional tabs 34 extend from the flange 17 and are inserted into slits 35 provided in the flange 33 of the outer box-shaped body 13.

It must be noted that the shank 32 of the rotor 27 besides being rotating is also axially sliding into the central axial hole 31 of the outer box-shaped body 13 so as to be able to move close to the partition wall 22 of the cylindrical element 16 being part of the inner box-shaped body 12 so as to interact with biological material to be ground. Furthermore the shank 32 of the rotor 27 axially provides a shaped hole 36 adapted to receive an end of a control element, as a shaped bit of a powered tool for example a "screwdriver".

In particular, the biological material 11 can be sampled directly in the operating room and submitted to comminuting in the comminuting device 11. Advantageously, the comminuting device according to the present invention can comprise or be associated to an adapter adapted to be mechanically coupled with a powered tool for rotating movable cutting elements.

Figure 19:
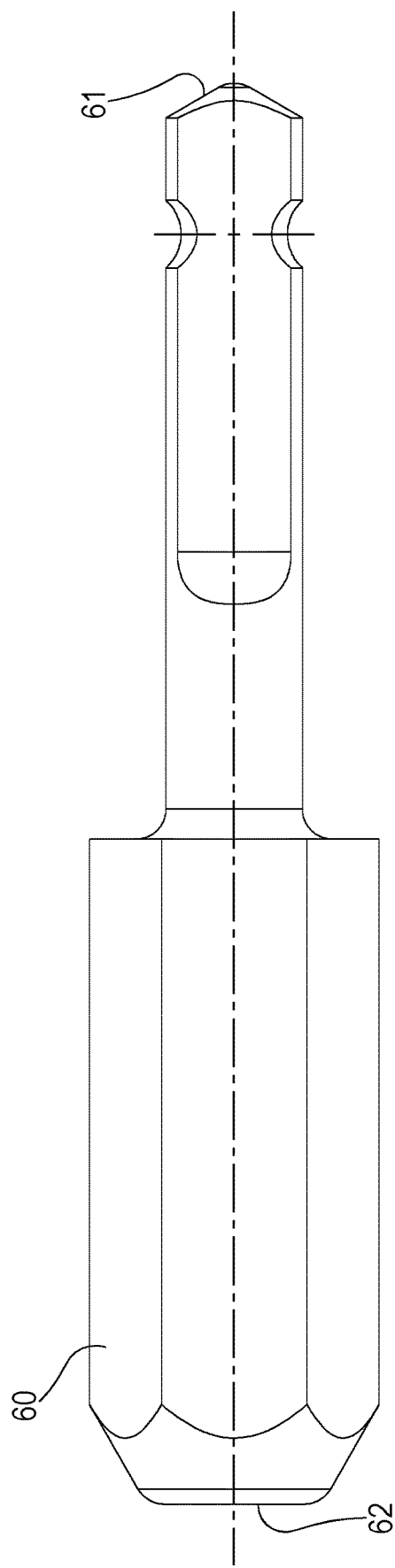
FIG. 19 is a longitudinal view of an adapter for a comminuting device.
Figure 20:
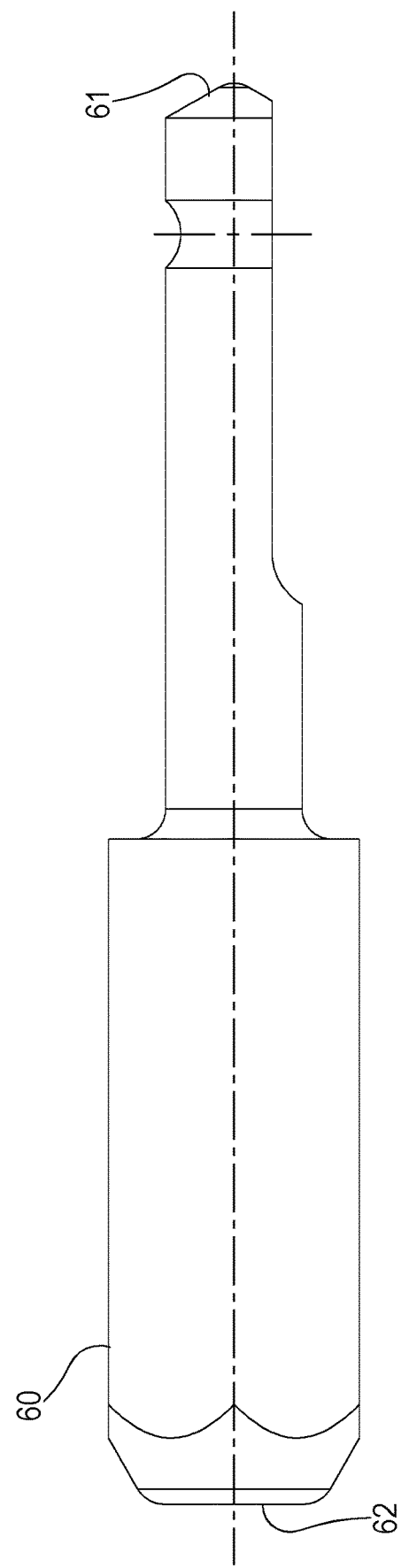
FIG. 20 is a second longitudinal view of the adapter of FIG. 19.

In FIGS. 19 and 20 an embodiment of the adapter indicated by reference number 60 is shown; the adapter 60 has a first end 61 adapted to be inserted into the shaped hole 36 and a second end 62 adapted to be reversibly associated to the powered tool; in particular, the first end 61 has a complimentary shape with respect to the shape of the shaped hole 36, while the second end 62 is shaped so as to be temporarily secured to the powered tool; in the figures, it must be noted that the first end 61 has, in section, greater dimension than the second end 62.

In particular, in the specific embodiment of FIG. 19 and FIG. 20, the first end 61 has a hexagonal shape and the distance between two opposite faces is substantially of 8.0 mm, while the second end 62 has a circular-plated section whose arc has a diameter of 4.5 mm, corresponding to the standard diameter of the powered tools used in the operating room. More specifically, the chord of the section with circular segment of the second end 62 is defined by a groove that extends in a longitudinal direction, partially extending from the second end 62 towards the first end 61.

In particular, the first end 61 and the second end 62 have a pilot hole, for example a countersink of the edges of the transversal section, to ease inserting the ends into respective seats.

Advantageously, the adapter 60, or a similar one, can be temporarily replaced to the standard shaped bit of an operating room powered tool.

By observing the figures, it can also be noted that the outer box-shaped body 13 provides at least a pass-through hole 37, obtained in a direction parallel to the axis of the outer box-shaped body 13, that can be aligned to at least a pass-through channel 38 obtained in the cylindrical element 16 being part of the inner box-shaped body 12. Such at least a channel 38 realises a connection between the outside of the device of the present invention and a collecting chamber 39 of the biological material, once ground as desired.

Figure 3:
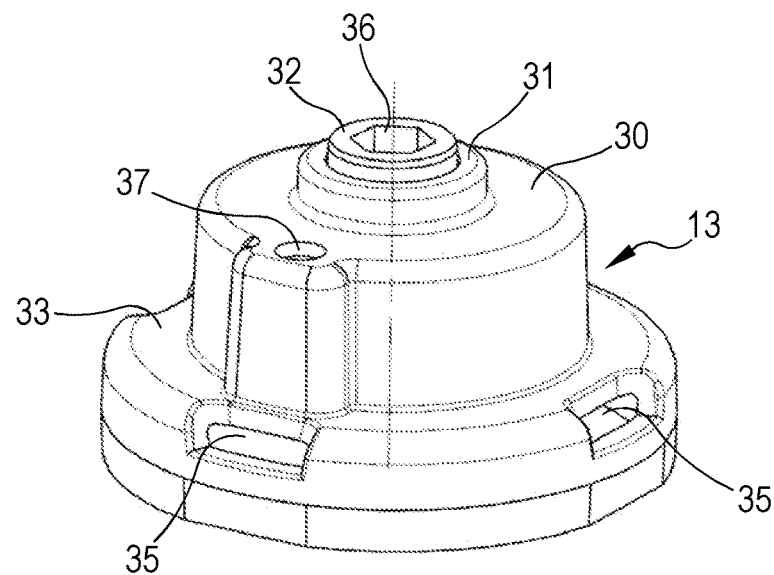
FIG. 3 is a perspective view of the comminuting device of FIG. 2 exploded into its two main parts.
Figure 3:
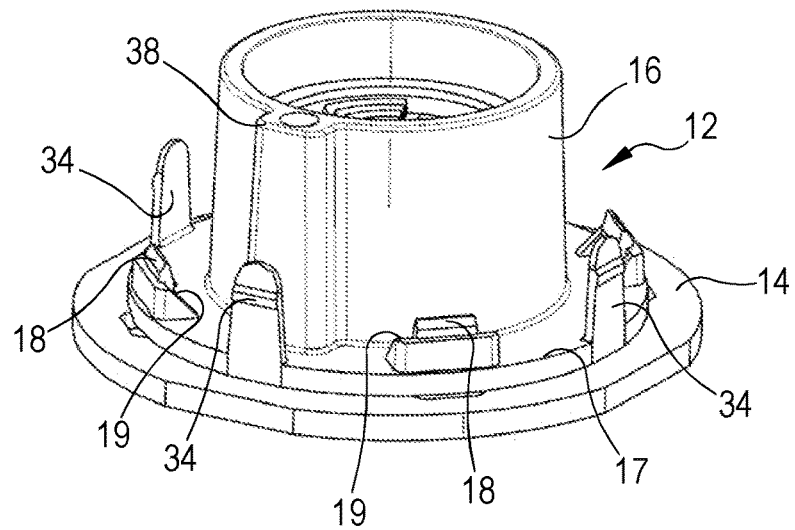
Figure 4:
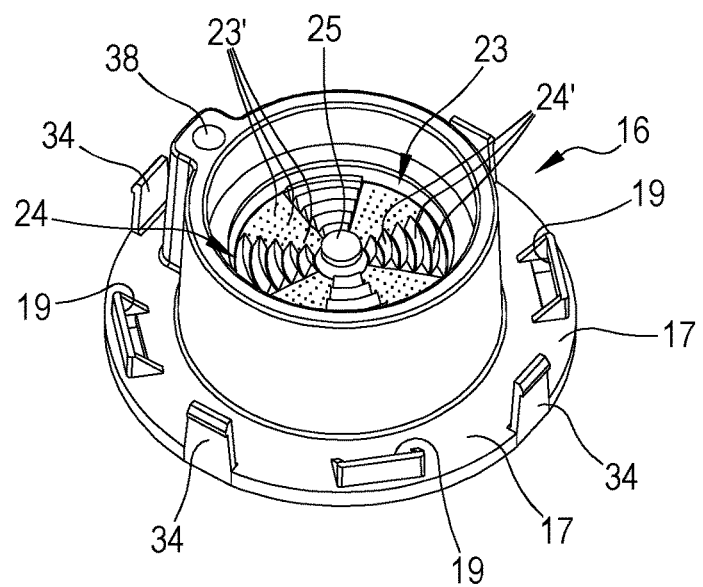
FIG. 4 is a perspective view according to a different angle of a portion with hollow cylindrical element of the lower part of what illustrated in FIG. 3.
Figure 5:
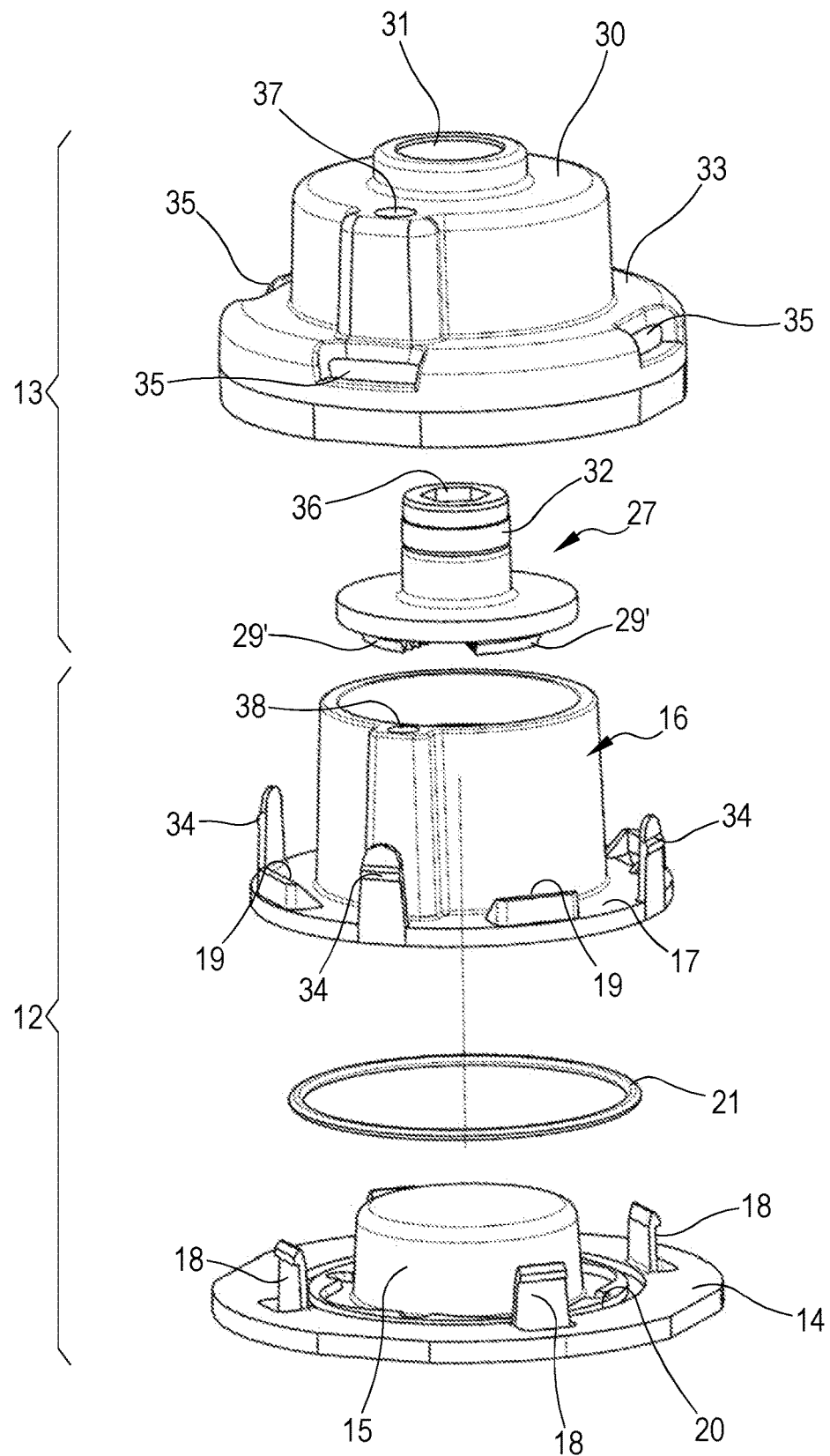
FIG. 5 is a perspective view of the comminuting device of FIG. 2 with its parts completely exploded.
Figure 6:
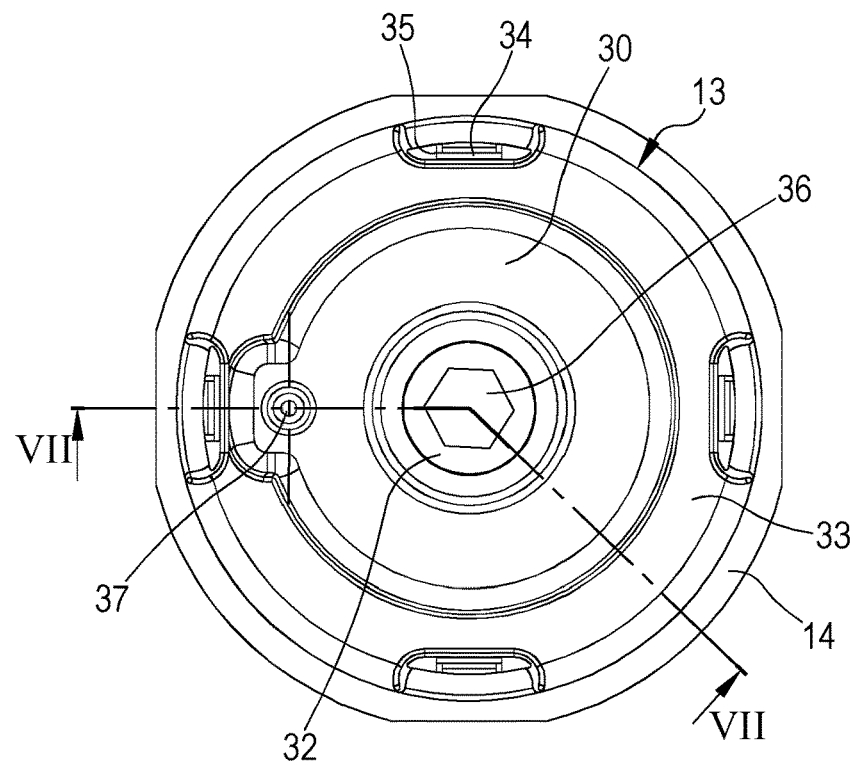
FIG. 6 is a plan view from above of the comminuting device of FIG. 2.
Figure 7:
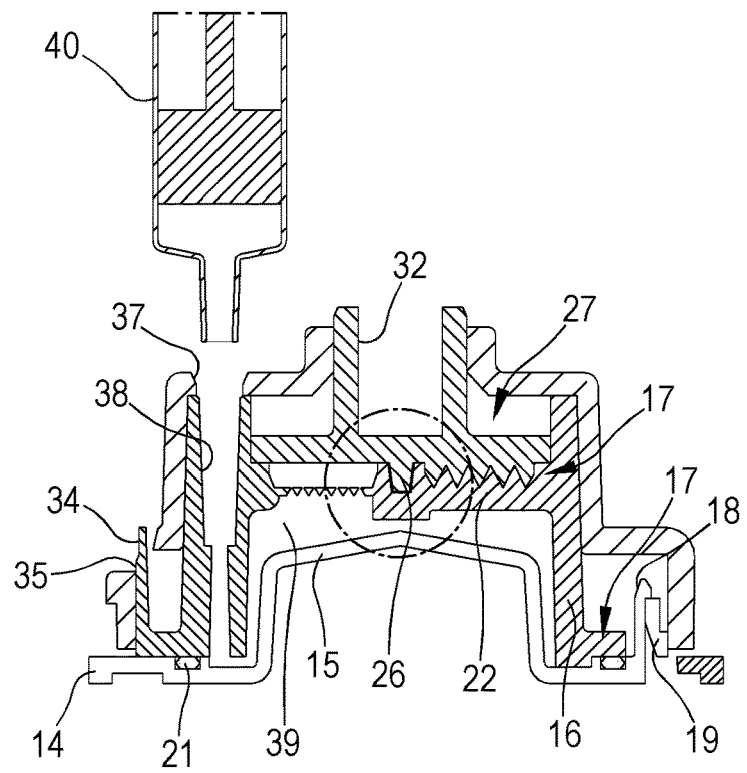
FIG. 7 is a section view of the comminuting device of the invention along the line VII-VII of FIG. 6 in an operative position.
Figure 8:
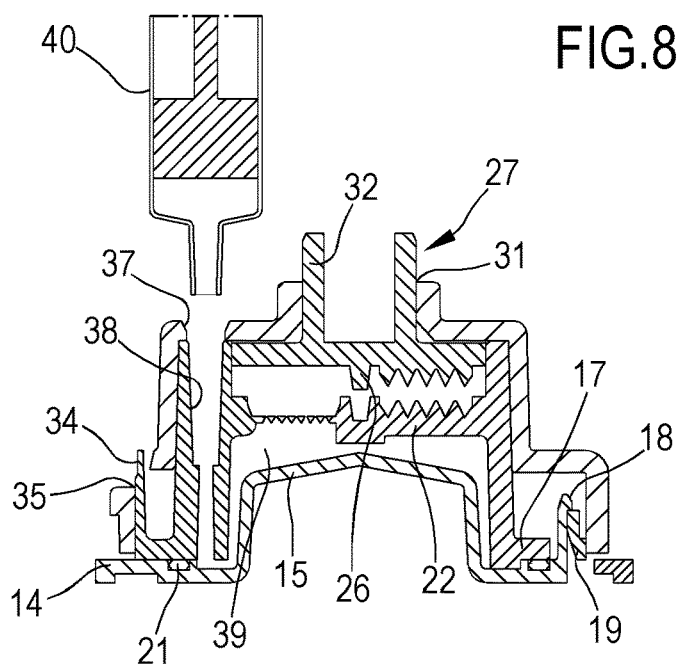
FIG. 8 is a section view of the comminuting device of the invention along the line VII-VII of FIG. 6 in a not yet operative initial position with disengaged spaced teeth.
Figure 9:
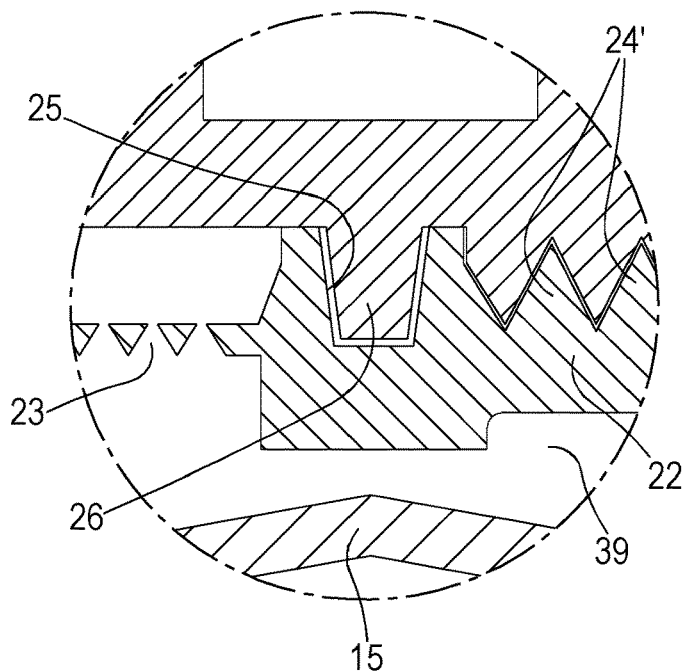
FIG. 9 is an enlarged section view of a detail of the comminuting device as shown in FIG. 6.
Figure 10:
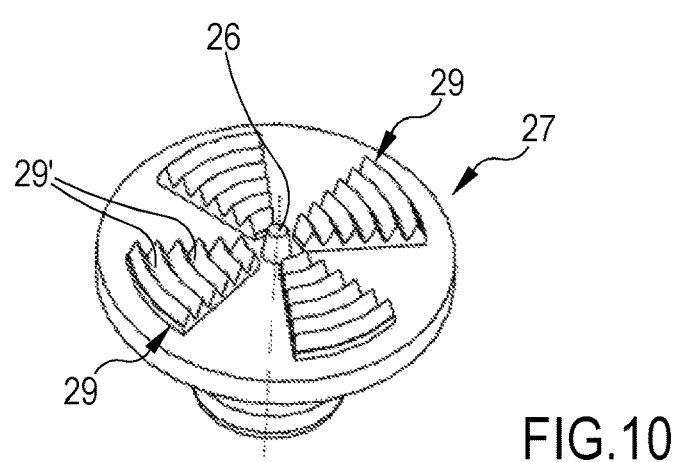
FIG. 10 is a perspective view according to a different angle of the only rotor as illustrated in FIG. 5.

In this first illustrated and described embodiment, the comminuting device 11 is provided to the user with the open casing as shown in FIG. 3 namely with the inner box-shaped body 12 (which typically, in use, is adapted to be arranged on top) and the outer box-shaped body 13 (which typically, in use, is adapted to be arranged on top) separated. Obviously as regards the inner box-shaped body 12 it provides that the hollow cylindrical element 16 is made integral with the base, with circular plate 14 inserting the tabs 18 into the slits 19 provided in the flange 17, once the O-ring 21 is placed in the annular housing 20. Similarly, the rotor 27 must have been housed in the outer box-shaped body 13 with the shank 32 housed in the central hole 31.

In a following step, the inner box-shaped body 12 is fixed to the base 10.

In a still following step, the biological material to be ground is arranged above the partition wall 22 of the cylindrical element 16.

At this time, the outer box-shaped body 13 is locked on the inner box-shaped body 12.

In a still following step, a saline solution with lubricating action is introduced during the following step of grinding the biological material to be treated. Such solution is introduced for example by a syringe 40 thanks to the presence of a pass-through hole 37 in the outer box-shaped body 13 and/or of the pass-through channel 38 obtained in the cylindrical element 16 and is arranged in the collecting chamber 39 of the biological material. The solution is introduced in an amount so as to overcome the height of the teeth 29' of sectors 29 and of the teeth 24' of sectors 24 and to wet the biological material to be ground; this is advantageous as it allows at the same time to avoid overheating the biological material and pushing the ground material towards the collecting chamber 39.

At this time, a powered tool bit (not shown) is inserted in the shaped hole 36 of the shank 32 of the rotor 27 to actuate the rotation control (for a given time and at a given speed).

The rotation results in comminuting the biological material, thanks to the presence of the saline solution, and such ground/comminuted material, once reached the required dimension, passes through the calibrated holes 23' of sectors 23 of the partition wall 22.

Figure 11:
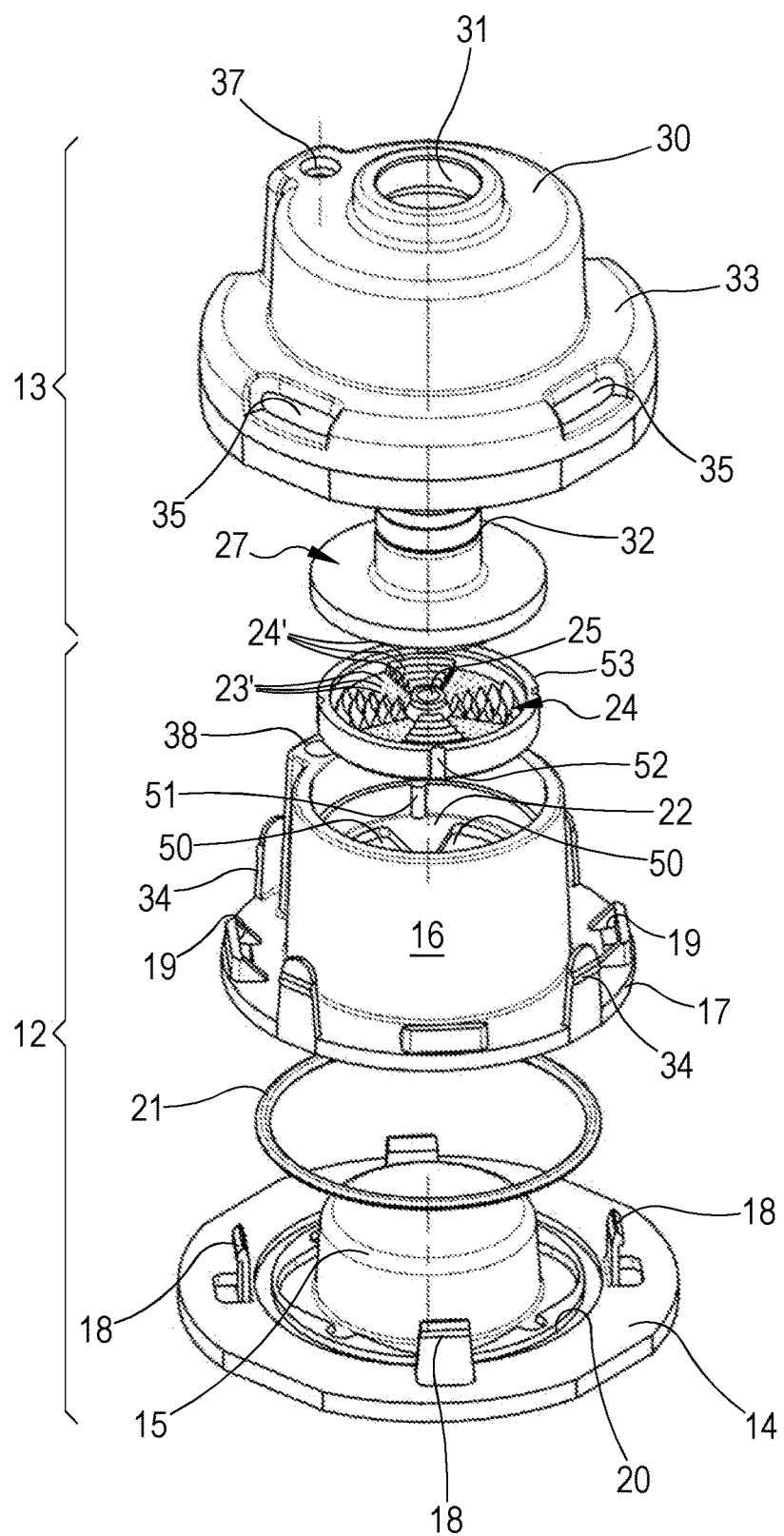
FIG. 11 is a perspective view of a second embodiment of a comminuting device according to the invention with its parts completely exploded.
Figure 12:
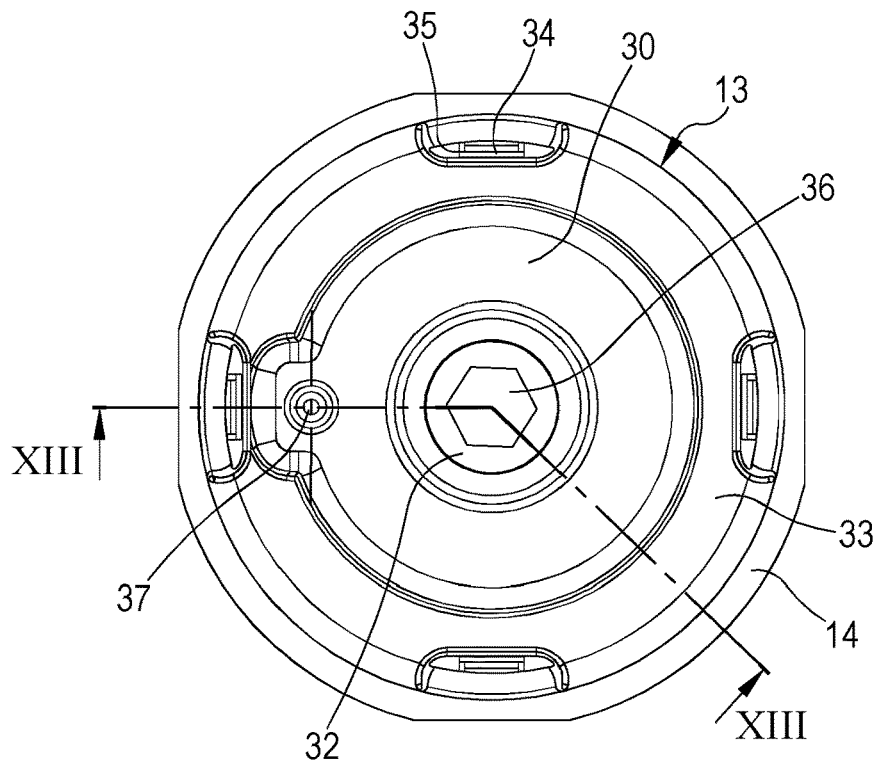
FIG. 12 is a plan view from above of the comminuting device of FIG. 11.
Figure 13:
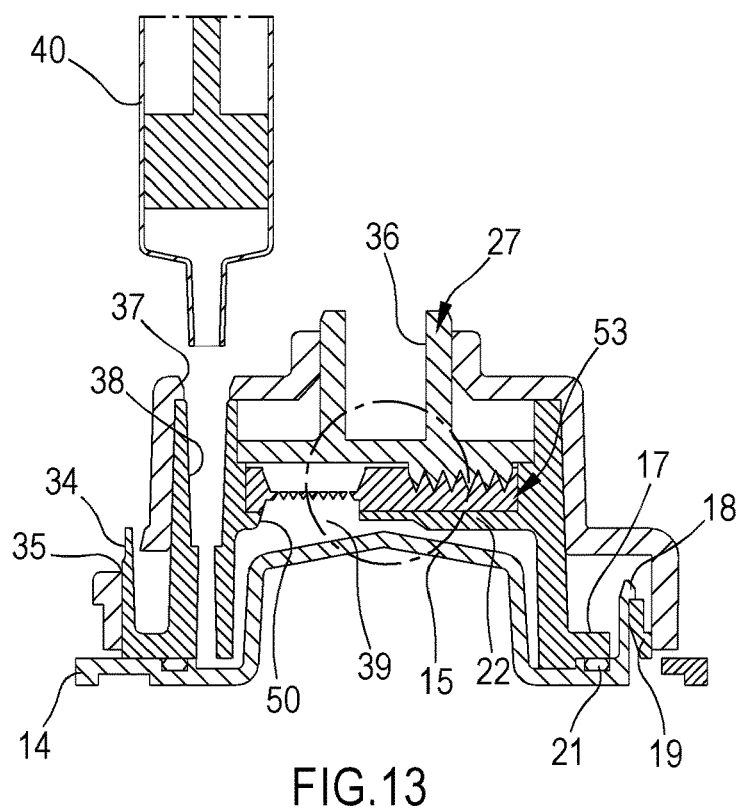
FIG. 13 is a section view of the comminuting device of the invention along the line XIII-XIII of FIG. 12 in an operative position.
Figure 14:
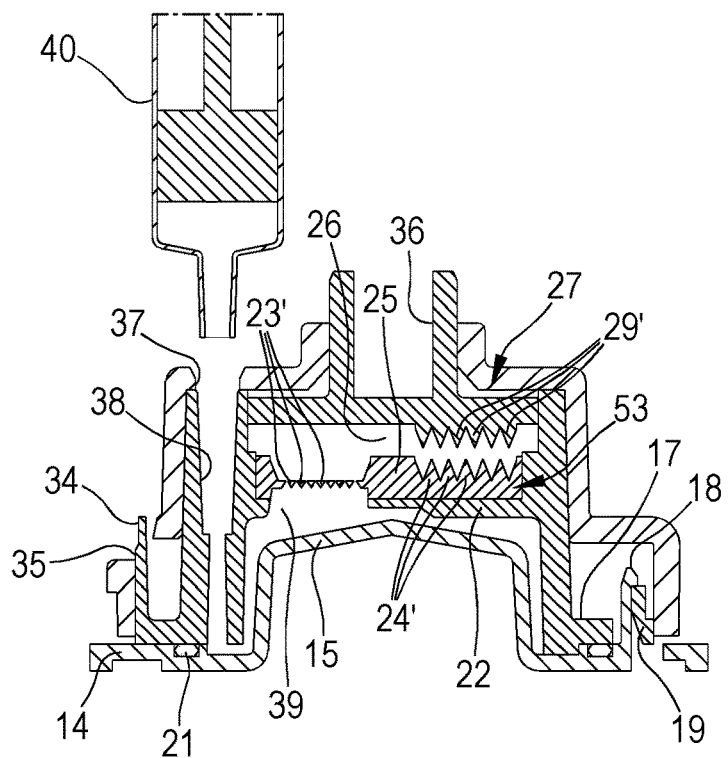
FIG. 14 is a section view of the comminuting device of the invention along the line XIII-XIII of FIG. 12 in a not yet operative initial position with disengaged spaced teeth.
Figure 15:
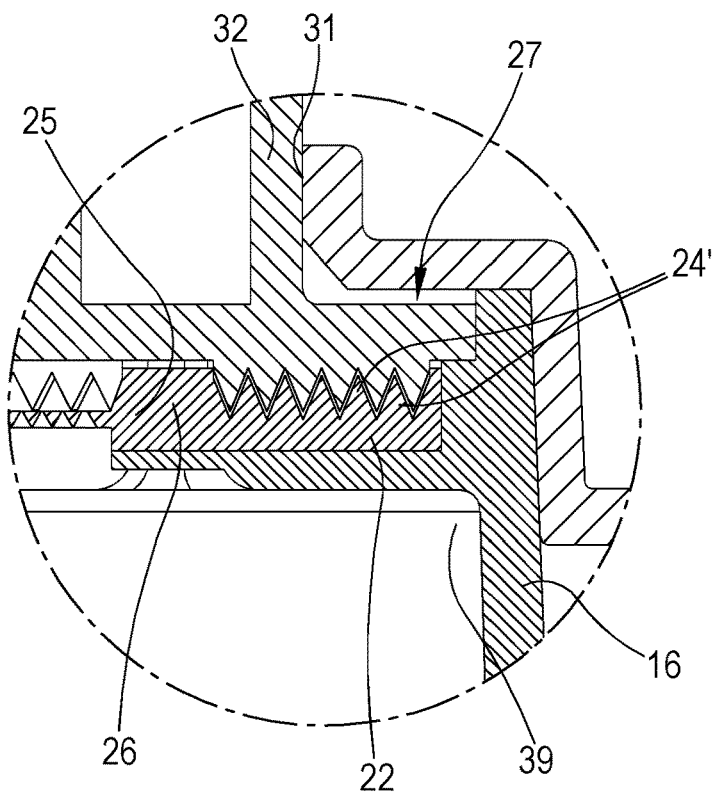
FIG. 15 is an enlarged section view of a detail of the comminuting device as shown in FIG. 13.

Once the grinding treatment is over, it is possible to extract such material by an additional syringe 40 introducing it into the pass-through hole 37 of the outer box-shaped body 13 and into the pass-through channel 38 aligned thereto and obtained in the cylindrical element 16. The treated and ground biological material is thus sucked from the collecting chamber 39 to be used in following steps/applications. FIGS. 11 to 15 show views of a second embodiment of a comminuting device according to the invention, in particular FIG. 11 shows such device with its parts completely exploded.

Where possible, even in this embodiment similar parts are indicated by same reference numbers.

It is observed that also in this example there are substantially an inner box-shaped body 12 and an outer box-shaped body 13 that can be associated with each other. Similarly the inner box-shaped body 12 comprises in a first part a base 14, with a circular plate, centrally provided with a camber 15, facing the upper outer body and facing the inside. In a second part the inner box-shaped body 12 comprises a hollow cylindrical element 16 also provided with a flange 17, radially facing the outside and obtained at an end of the cylindrical element 16 facing the base 14. The base 14 can be associated to the flange 17 and it is constrained thereto by means of snap-on elements 18 in form of tabs. The tabs 18 extend from the base 14 and are inserted into slits 19 provided in the flange 17. Around the camber 15 of the base 14 an annular housing 20 is obtained adapted to receive an O-ring 21 that, when engaged with a lower surface of the flange 17, realises the mentioned collecting chamber of the biological material, once cut.

In this second embodiment of FIGS. 11 to 15, in an intermediate inner portion of the cylindrical element 16 a partition wall 22 is arranged provided with windows 50 in the form of radial sectors. Above such partition wall 22 on an inner wall of the cylindrical element 16 short ridges 51 are obtained that protrude radially towards the inside and axially directed. And such protruding ridges 51 engage within complimentary recesses 52 obtained on a side surface of a separate disc 53 placeable above the partition wall 22. In particular such disc 53 is divided in sectors which provide alternatively sectors 23 provided with a set of calibrated holes 23' and sectors 24 provided with concentric arc-of-a-circle teeth 24'. Both sectors 23 provided with a set of calibrated holes 23' and sectors 24 provided with concentric arc-of-a-circle teeth 24' converge centrally towards a central circular seat 25 in the disc 53 and face a rotor 27 housed inside and being part of the outer box-shaped body 13.

In this embodiment it is important to note that thanks to cooperating ridges 51 and recesses 52 the sectors 23 provided with the set of calibrated holes 23' are arranged at the windows 50 of the partition wall 22 to allow the passage of the biological material, once cut, towards the underlying collecting chamber 39 as in the first example.

According to the embodiment of FIGS. 11-15, the rotor 27 with its cutting elements is made in a single piece of metal material (for example stainless steel or titanium) and the partition wall 22 with its cutting elements integrated for example into the disc 53 is made in two pieces, in particular the wall is made of plastic material and cutting elements are made of metal material (for example stainless steel or titanium); this embodiment is in particular for grinding bone material.

All the other remaining characteristics of the device in this second embodiment are similar or very similar.

As a matter of fact, the mentioned central circular seat 25 identifies a housing for a shaft piece 26 extending from the aforesaid rotor 27. The rotor 27 provides in a surface thereof facing the disc 53 a set of sectors 29 provided with concentric arc-of-a circle teeth 29' where such sectors 29 are complimentary as for shape to sectors 24 provided with concentric arc-of-a circle teeth 24' of the disc 53 which is placed above the partition wall 22 of the cylindrical element 16.

In this case also the outer box-shaped body 13 can be arranged to surround at least partially the inner box-shaped body 12 which, in a first end thereof closed by a wall 30, provides an axial central hole 31 that defines a housing seat and rotation of a tang 32 of the rotor 27.

Furthermore, the outer box-shaped body 13 provides at the other end thereof a shaped flange 33 radially protruding outwards and such to abut the base 14, with circular plate.

It must be noted that the flange 17 of the cylindrical element 16 also provides snap-on elements 34 in form of tabs. Such additional tabs 34 extend from the flange 17 and are inserted into slits 35 provided in the flange 33 of the outer box-shaped body 13.

In addition it must be noted that the shank 32 of the rotor 27 besides being rotating is also axially sliding into the central axial hole 31 of the outer box-shaped body 13 so as to be able to move close to the disc 53 arranged blocked on the partition wall 22 of the cylindrical element 16 being part of the inner box-shaped body 12 so as to interact with biological material to be ground. Furthermore the shank 32 of the rotor 27 provides axially a shaped hole 36 adapted to receive an end of a control element, such as a shaped bit of a powered tool for example a "screwdriver".

By observing the figures, it can also be noted that the outer box-shaped body 13 provides at least a pass-through hole 37, obtained in a direction parallel to the axis of the outer box-shaped body 13, that can be aligned to at least a pass-through channel 38 obtained in the cylindrical element 16 being part of the inner box-shaped body 12. Such at least a channel 38 realises a connection between the outside of the device of the present invention and a collecting chamber 39 of the biological material, once cut as desired.

In this second illustrated and described embodiment, the comminuting device 11 is provided to the user with an inner box-shaped body 12, outer box-shaped body 13 and disc 53.

Figure 16:
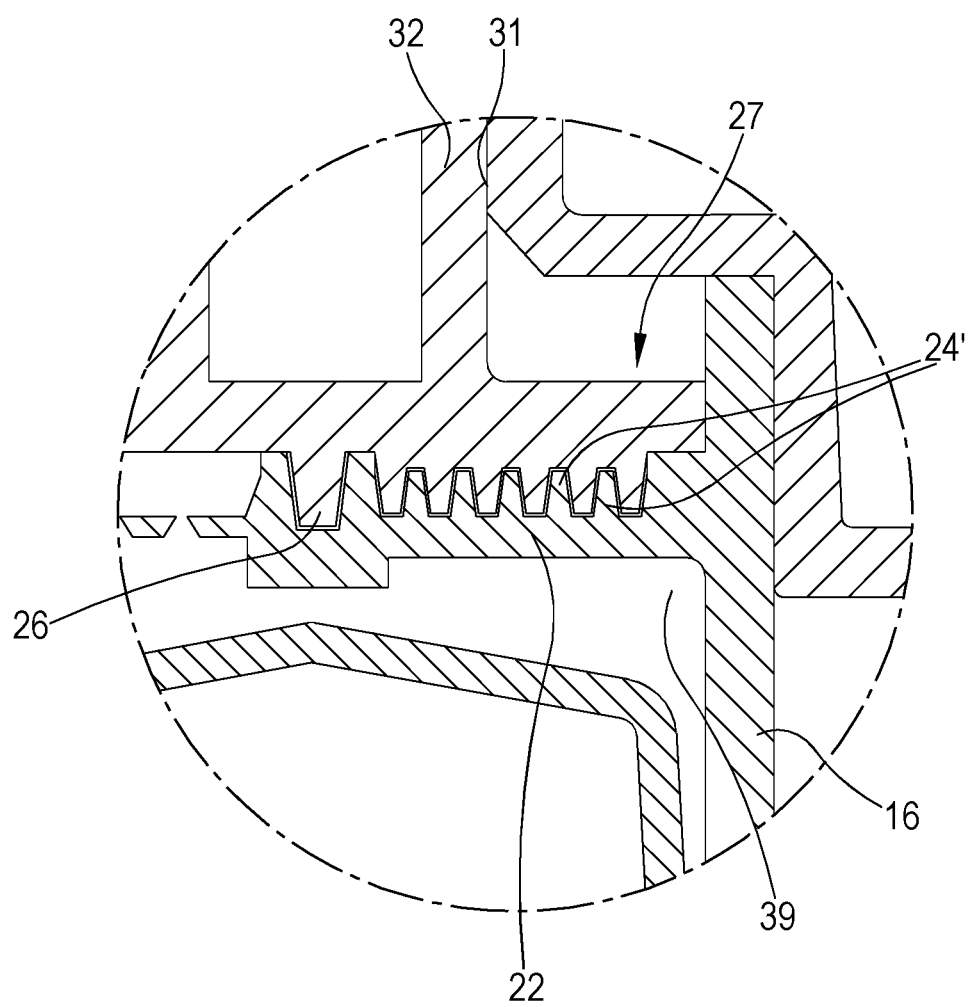
FIG. 16 is a section view of the comminuting device of the invention in a further embodiment in a not yet operative position with disengaged spaced teeth.

FIG. 16 shows that in a further alternative embodiment, the concentric arc-of-a circle teeth of the sectors of either the partition wall 22 and the disc 53 can have for example a trapezoidal section instead of the substantially triangular one shown in the previous examples. In this case such sectors are indicated by 124 and teeth are indicated by 124' to distinguish them from the previous ones, while the remaining reference numbers stay unchanged.

Figure 17:
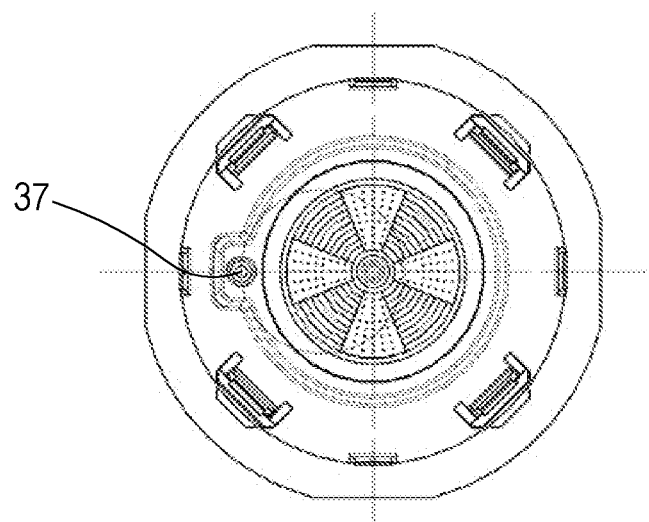
FIG. 17 is a plan view from above of a lower part of a comminuting device.
Figure 18:
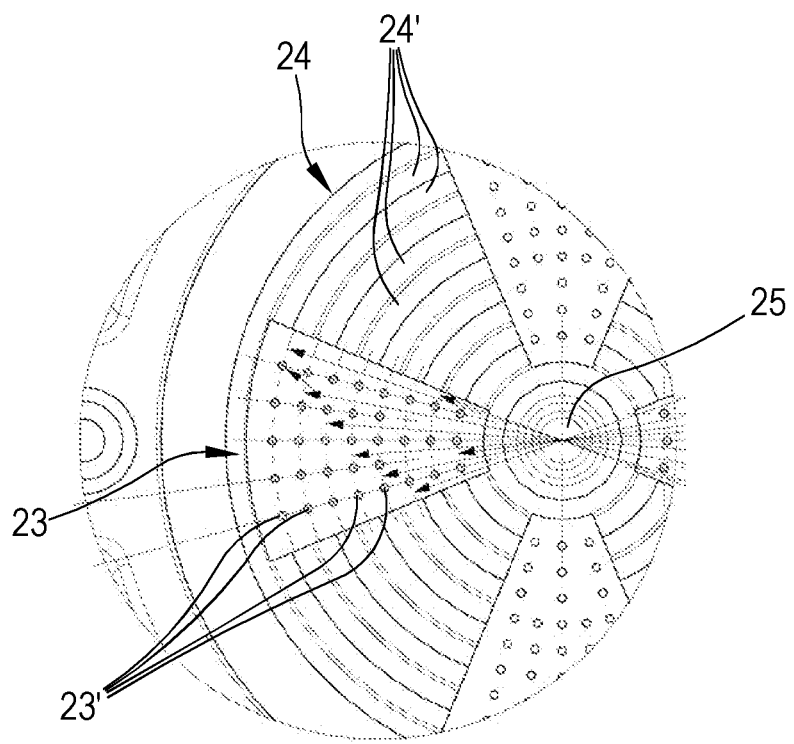
FIG. 18 is an enlarged detail of the plan view from above of a lower part of a comminuting device of FIG. 17.

Finally FIGS. 17 and 18 detail more clearly what the arrangement of the sectors is either in case they are made in the partition wall 22 and in case they are made in the disc 53.

Comminuting devices as the ones just described implement a particular method for comminuting a biological material which is the object of the present invention. In general, such method is based on a comminuting device provided with fixed cutting elements (for example elements 24') and movable cutting elements (for example elements) complimentary in shape, and with the steps of:

A) manually placing biological material to be ground between the fixed cutting elements and the movable cutting elements angularly spaced apart,
then
B) rotating the movable cutting elements according to a direction of rotation so as to move the movable cutting elements close to the fixed cutting elements until they are aligned to each other,
then
C) further rotating the movable cutting elements according to the same direction of rotation so as to angularly space the movable cutting elements from the fixed cutting elements;

The steps A, B and C are repeated several times so as to generate ground biological material;

In step B upon mutual alignment, the movable cutting elements and the fixed cutting elements have a predetermined distance (ranging for example from 100 to 500 μm, preferably from 200 to 400 μm, and which is more preferably equal to 300 μm) in an axial direction.

Cutting biological material conceptually occurs when the cutting elements align to each other (very precise, clean and homogeneous cut), but it actually starts shortly before the step B when the cutting elements are close (for example at a distance of 1 or 2 cm) and stops shortly after in the step C when the cutting elements are close (for example at a distance of 1 or 2 mm).

In the case of the described comminuting devices, during the step C, the sectors (for example 29) provided with rotor teeth (for example 27) superimpose increasingly more with sectors (for example 24) provided with teeth of the partition wall (for example 22).

In the case of the described comminuting devices, thanks to the symmetrical shape of the sectors of the partition wall and of the rotor, the comminuting operation can be carried out by rotating in a first direction of rotation or rotating in a second direction of rotation (opposite to the first one) or alternating the first direction of rotation and the second direction of rotation.

Preferably and as already explained, the biological material to be ground, the fixed cutting elements and the movable cutting elements are immersed in a saline solution during the steps B and C. In the case of the described comminuting devices, such saline solution is introduced into the device at the beginning of a process and extracted from the device at the end of the process and the extracted solution also contains the ground biological material (or at least a great part thereof).

Preferably, the biological material already ground thanks to the action of cutting elements is passed through calibrated holes (with a diameter ranging from 100 to 500 μm, preferably from 200 to 400 μm, and which is more preferably equal to 300 μm) on a wall; such holes make it possible for the biological material already ground by the comminuting device to have predetermined dimensions.

According to a first advantageous aspect of the method according to the present invention, the biological material to be ground is wet and is kept wet by a saline solution while being ground.

According to a second advantageous aspect of the method according to the present invention, the ground biological material is transported through the calibrated holes preferably by a saline solution.

According to a third advantageous aspect of the method according to the present invention, the ground biological material is preferably removed by means of a saline solution.

In the case of the described comminuting devices, these three advantageous aspects are obtained as follows; a saline solution is introduced into the device, then reaches the collecting chamber and finally passes through the calibrated holes of the partition wall reaching the biological material to be ground as well as the relative cutting elements. Then, the rotor is driven (either manually or electrically), the material is gradually ground and thanks to the pressure exerted by the rotor on the saline solution during the rotor rotation, the ground biological material is dragged by the saline solution through the calibrated holes into the collecting chamber. Finally, the rotor is stopped, and the saline solution with the ground biological material present in the collecting chamber (i.e. a "preparation of comminuted cellular material suspended in the saline solution") is extracted from the device.

In the case of some embodiments, the rotation speed of the rotor is comprised between 70 and 100, preferably 80 rpm, and the rotor is rotated for a time ranging from 100 and 200 seconds, preferably for 120 seconds.

The comminuting device, adapted to comminute a biological material to obtain samples or specimens to be tested, according to the present invention is particularly advantageous as it performs an extremely precise, clean and homogeneous cut, obtaining cellular grafts with substantially homogeneous shape and dimensions.

The invention claimed is:

1. A comminuting device of biological material, comprising
   a casing that contains fixed cutting elements and movable cutting elements cooperating with each other to grind biological material,
   a collecting chamber for ground biological material,
   a partition wall adjacent to said collecting chamber,
      wherein said fixed and movable cutting elements are above said partition wall together with the biological material to be ground,
      said collecting chamber is below said partition wall,
      said fixed cutting elements are in the form of elongated corners that extend radially,
      said movable cutting elements are in the form of elongated corners that extend radially, and
      said partition wall is provided with wall portions,
   wherein calibrated holes are provided for the passage of biological material ground by said fixed cutting elements and said movable cutting elements, said collecting chamber being in connection with the outside of said casing through at least a channel and a syringe for the introduction of liquid and the extraction of said liquid with ground biological material.

2. The comminuting device according to claim 1, wherein said casing comprises an inner box-shaped body and an outer box-shaped body, both shaped in a cylindrical form, where said fixed cutting elements are arranged in said inner box-shaped body and said movable cutting elements are arranged on a rotor, which is free at least to rotate in said outer box-shaped body.

3. The comminuting device according to claim 2, wherein said inner box-shaped body and said outer box-shaped body of said casing are engaged with each other by means of snap-on elements.

4. The comminuting device according to claim 2, wherein said fixed cutting elements are arranged on said partition wall.

5. The comminuting device according to claim 2, wherein said fixed cutting elements are arranged on a separate disc, which can be placed above said partition wall.

6. The comminuting device according to claim 1, wherein said fixed cutting elements are arranged in a first sector and said movable cutting elements are arranged in a second sector.

7. The comminuting device according to claim 1, wherein said calibrated holes are arranged in sectors.

8. The comminuting device according to claim 7, wherein said sectors having said calibrated holes are arranged alternately in sectors having said fixed cutting elements.

9. The comminuting device according to claim 2, wherein said inner box-shaped body comprises, in a first part, a base, with a circular plate, centrally provided with a camber facing towards said outer box-shaped body and towards the inside, and, in a second part, a hollow cylindrical element equipped with a flange, facing radially outwards and obtained from one end of said hollow cylindrical element facing said base and arranged so as to be sealed with respect thereto.

10. The comminuting device according to claim 9, wherein said base can be coupled to said flange and is constrained thereto by means of snap-on elements.

11. The comminuting device according to claim 10, wherein said snap-on elements are on one side tabs and on the other, slits.

12. The comminuting device according to claim 9, wherein around said camber of the base, an annular housing, able to receive an O-ring, is obtained, which when engaged by a lower surface of the flange, realises the aforementioned collecting chamber of biological material, once cut.

13. The comminuting device according to claim 1, wherein said collecting chamber is connected to the outside by means of through openings obtained from said casing.

14. A method for comminuting a biological material by means of a comminuting device of claim 1, comprising the steps of:
A) manually placing biological material to be ground between said fixed cutting elements and said movable cutting elements angularly spaced apart,
then
B) rotating said movable cutting elements according to a direction of rotation so as to move said movable cutting elements close to said fixed cutting elements until they are aligned to each other,
then
C) further rotating said movable cutting elements according to said direction of rotation so as to angularly space said movable cutting elements from said fixed cutting elements;
wherein steps A, B and C are repeated several times so as to generate ground biological material;
wherein in step B, upon aligning them to each other, said movable cutting elements and said fixed cutting elements have a predetermined distance in the axial direction.

15. The method according to claim 14, comprising the following steps:
introducing biological material to be comminuted in the comminuting device;
introducing a saline solution in the comminuting device;
comminuting the biological material immersed in the saline solution by operating the comminuting device at a speed between 70 and 100, for a time ranging from 100 to 200 seconds; and
sampling a preparation of comminuted cellular material in suspension in the saline solution.

\* \* \* \* \*